(12) United States Patent
Ohara

(10) Patent No.: US 7,170,064 B2
(45) Date of Patent: Jan. 30, 2007

(54) RADIATION IMAGE GENERATING SYSTEM

(75) Inventor: Hiromu Ohara, Hachioji (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 41 days.

(21) Appl. No.: 11/179,913

(22) Filed: Jul. 12, 2005

(65) Prior Publication Data
    US 2006/0016998 A1    Jan. 26, 2006

(30) Foreign Application Priority Data
    Jul. 21, 2004  (JP) .............................. 2004-213011

(51) Int. Cl.
    *G01T 1/20* (2006.01)
(52) U.S. Cl. ...................... 250/370.11; 378/4
(58) Field of Classification Search ........... 250/370.11, 250/370.06, 370.09, 363.02; 378/4, 19, 98.8
    See application file for complete search history.

(56) References Cited

U.S. PATENT DOCUMENTS 4,415,982 A * 11/1983 Nishikawa ............. 250/363.02
6,396,898 B1 * 5/2002 Saito et al. .................... 378/19
6,515,286 B2 * 2/2003 Kuwabara .............. 250/370.11
6,760,404 B2 * 7/2004 Saito et al. ................ 378/98.8
2006/0054833 A1 * 3/2006 Tsuchino et al. ...... 250/370.11

* cited by examiner

*Primary Examiner*—Otilia Gabor
(74) *Attorney, Agent, or Firm*—Lucas & Mercanti, LLP

(57) ABSTRACT

A radiation image generating system, comprising: a plurality of radiation image detecting apparatuses, each including at least a scintillator layer having a scintillator to emit light according to an entered radiation, a photoelectric conversion layer to detect the light emitted by the scintillator to convert the detected light into electric energy, and a switching element layer having switching elements to accumulate and output the electric energy obtained by the photoelectric conversion layer, the radiation image detecting apparatuses obtaining radiation image information of a subject; and a radiation image generating operation control apparatus including a selection section to select a desired radiation image detecting apparatus among the plurality of radiation image detecting apparatuses, wherein the radiation image generating operation control apparatus includes a display section to display scintillator information of the scintillator used in each of the plurality of radiation image detecting apparatuses.

24 Claims, 7 Drawing Sheets

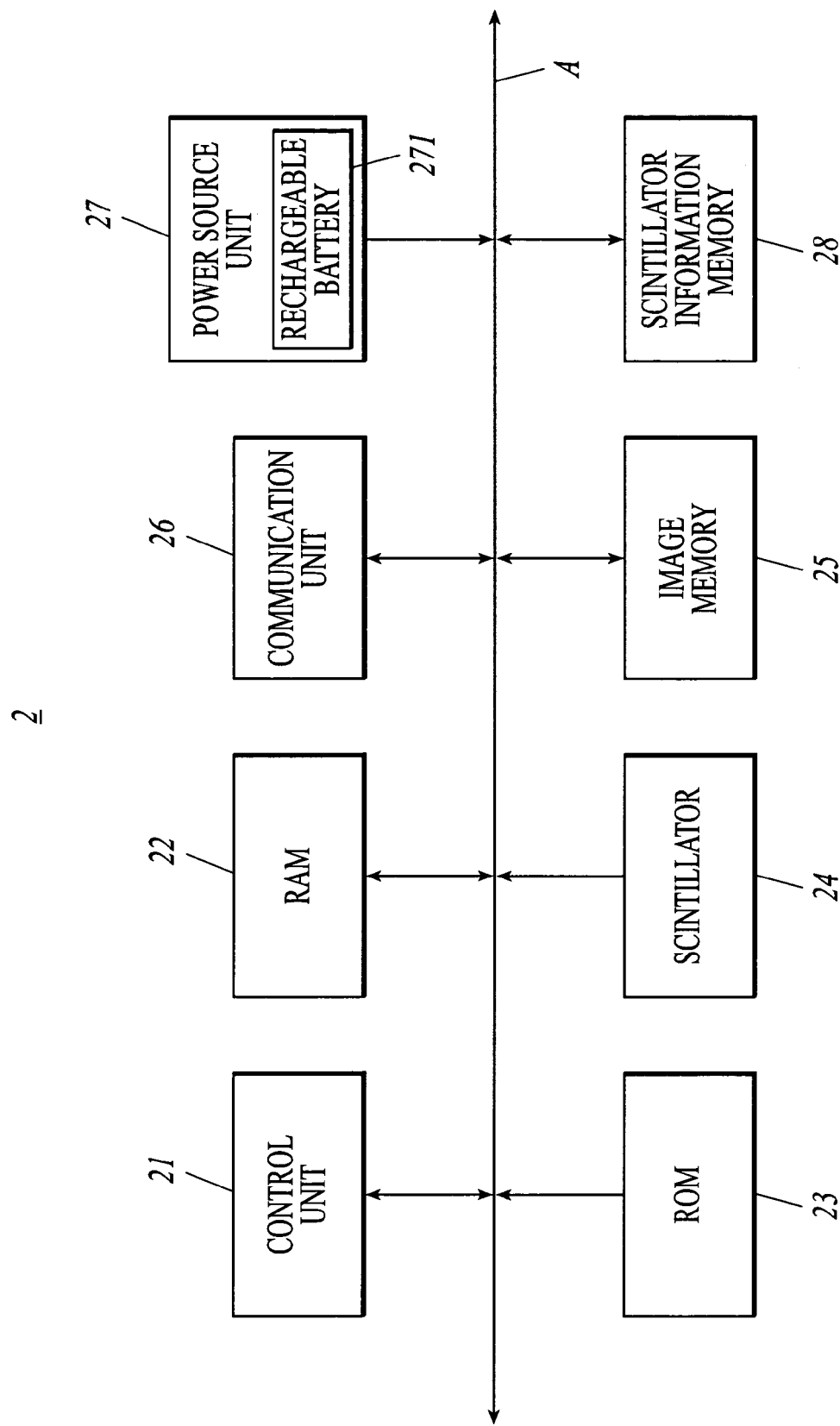

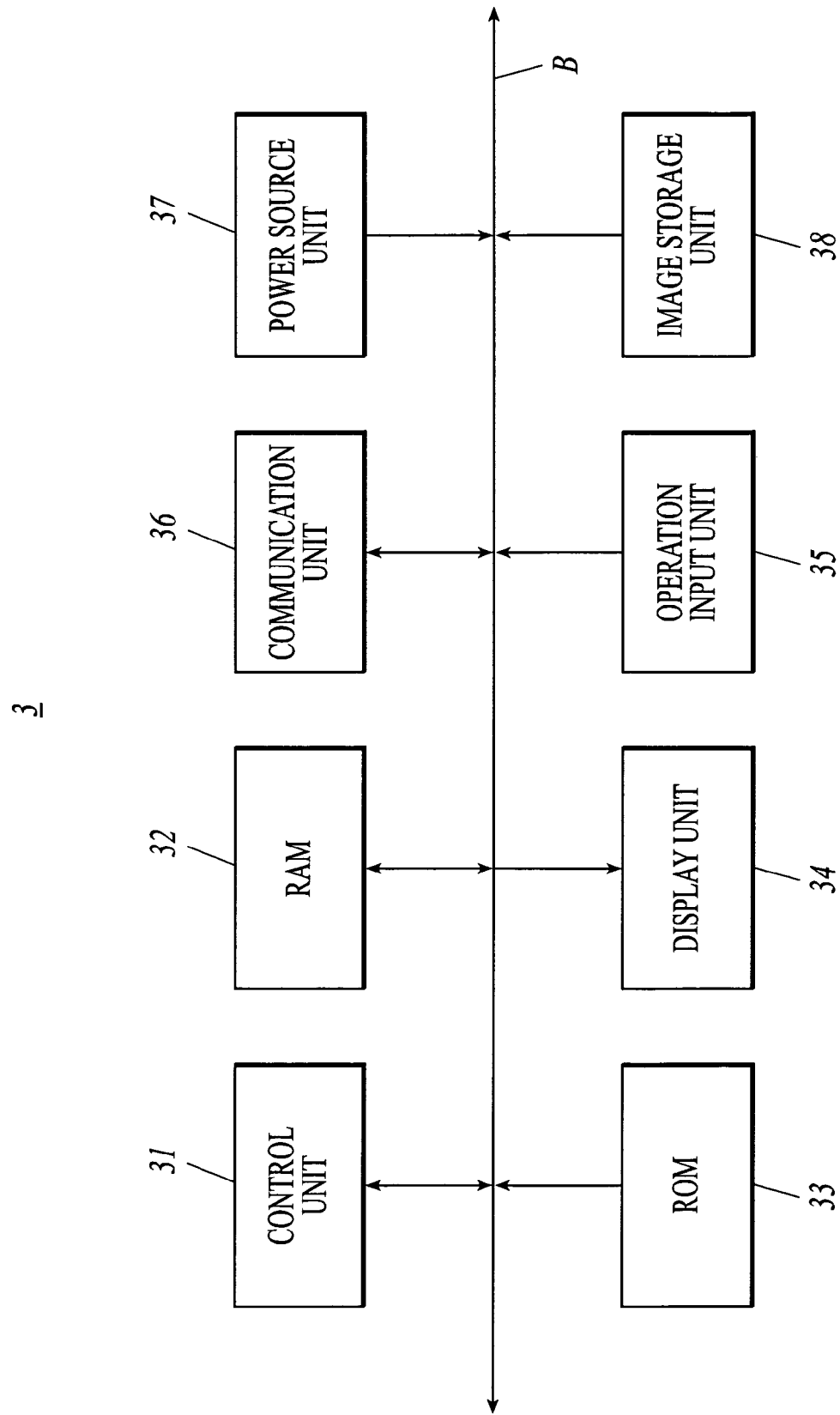

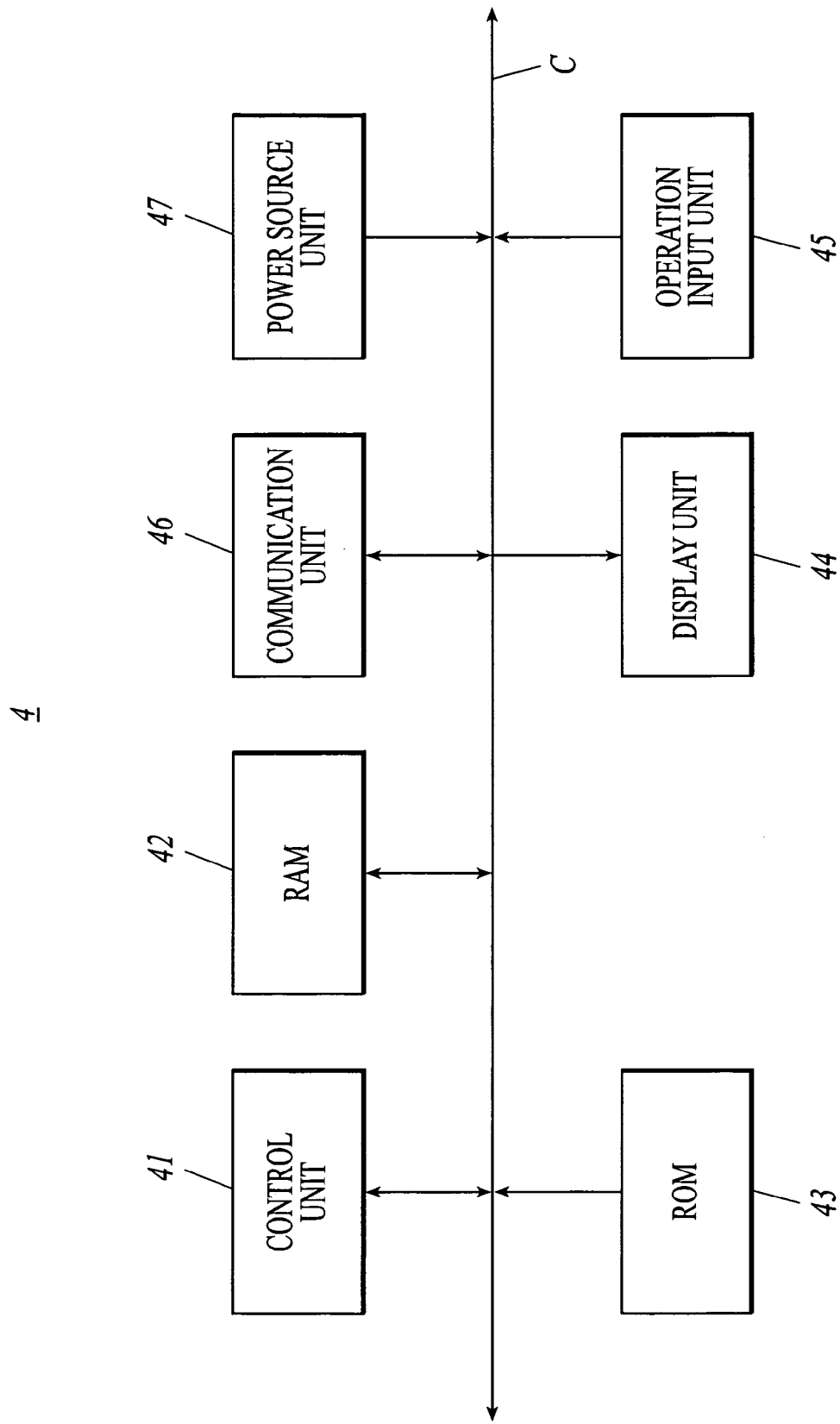

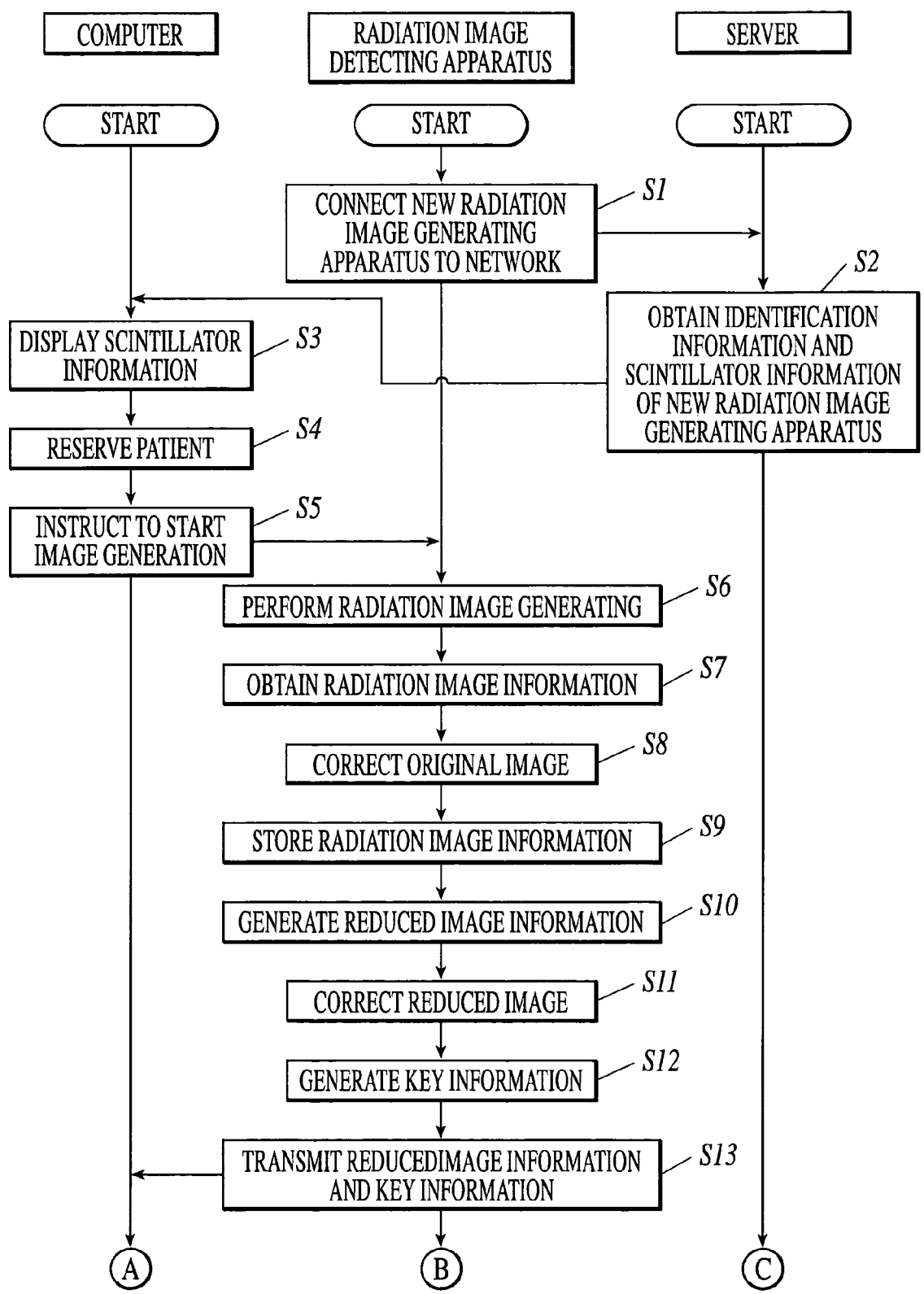

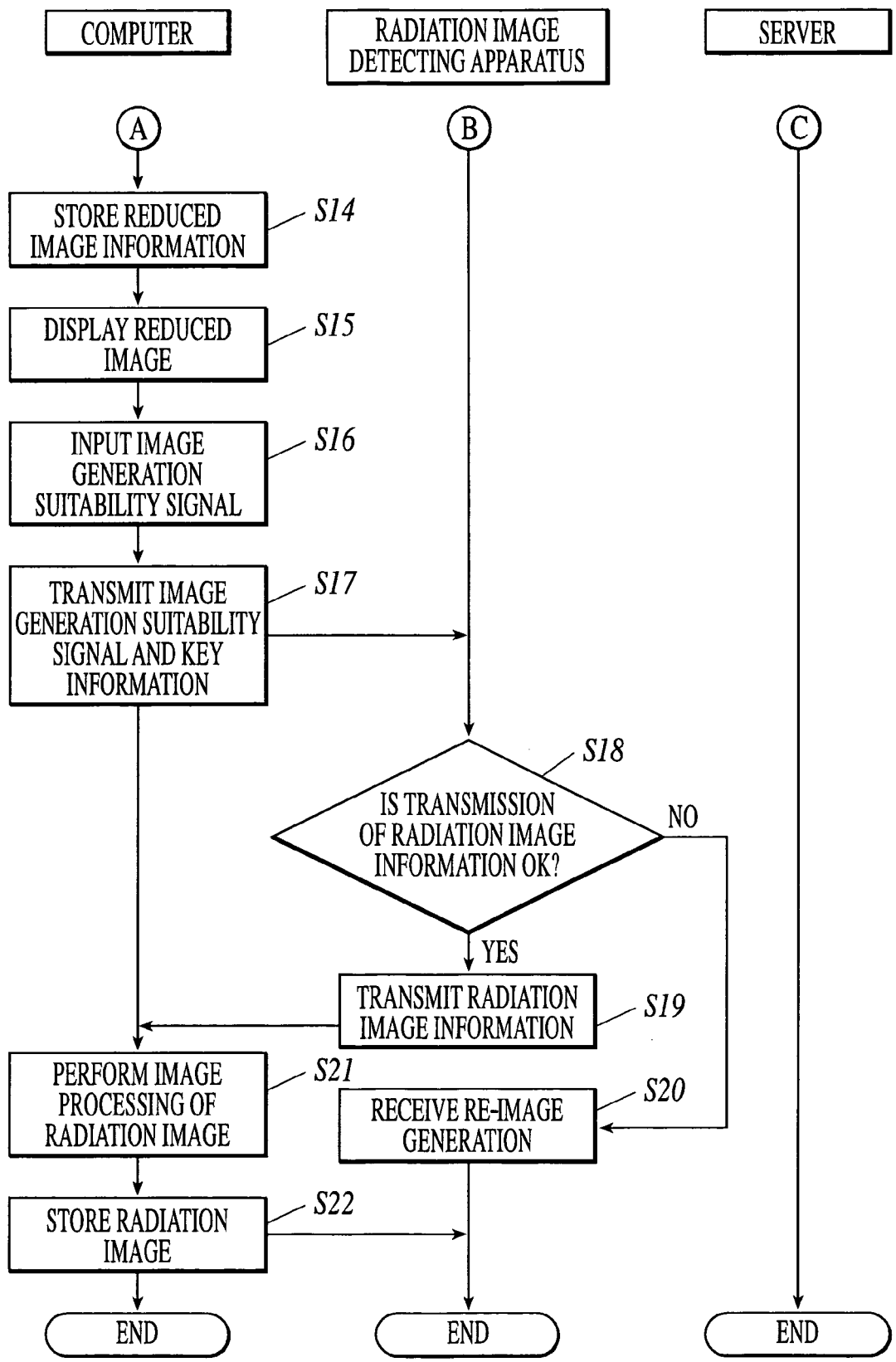

RADIATION IMAGE GENERATING SYSTEM

BACKGROUND OF THE INVENTION

1. Field of the Invention

The present invention relates to a radiation image generating system, particularly, to a radiation image generating system for generating a radiation image represented by an X-ray image.

2. Description of Related Art

Conventionally, in a medical diagnosis, a subject is irradiated with a radiation such as an X-ray, and a radiation image obtained by detecting an intensity distribution of the radiation which has penetrated the subject is widely used. In recent years, at the time of performing radiation image generation, a radiation image generating system using a flat panel detector (FPD) for detecting a radiation and converting the detected radiation to electric energy to detect the radiation as radiation image information has been proposed. A scintillator for detecting radiation intensity is mounted on the FPD.

In the radiation image generating system, there is one configured to use an FPD arranged in a radiation image generation room in connection with a predetermined radiation image generating operation control apparatus (controller) such as a personal computer (PC), for controlling radiation image generating operations through predetermined communication lines with an aim of improving the degree of freedom of the system configuration thereof (for example, refer to JP-Tokukai-2003-199736A).

A cassette type FPD containing an FPD in a cassette to improve the carrying property and the handling property of the FPD has been also developed (for example, refer to JP-Tokukaihei-6-342099A). Furthermore, a radiation image generating system in which a cassette type FPD and a radiation image generating operation control apparatus are configured as a system capable of communicating various kinds of information such as radiation image information by a radio system has been also proposed (for example, refer to JP-Tokukai-2003-210444A).

Generally, it is necessary to confirm whether image generation has been performed suitably or not after the image generation, and in the radiation image generating system described above, a radiation image is displayed on a computer. For example, in the above-described radiation image generating system disclosed in JP-Tokukai-2003-199736A, which is configured to connect the FPD and the radiation image generating operation control apparatus with each other through a communication line dedicated for the system, an image generation state can be confirmed by transmitting radiation image information from the FPD to the radiation image generating operation control apparatus, and by displaying reduced images such as thumbnail images produced on the basis of radiation images received by the radiation image generating operation control apparatus on a computer.

However, when the configuration in which the FDP and the radiation image generating operation control apparatus are connected with each other through the communication line dedicated for the system is adopted, the degree of freedom of the system configuration becomes low. Accordingly, it is considerable to build a system by connecting the FDP and the radiation image generating operation control apparatus with each other through an existing network such as Ethernet (registered trademark). However, in this case, communication of radiation image information takes much time, and it is difficult to perform confirmation of an image generation state immediately after the image generation.

Then, in the FPD, a radiation image generating system having a system configuration in which, after producing reduced image information having an information amount less than radiation image information, the produced reduced image information is transmitted to a radiation image generating operation control apparatus, and the reduced image is displayed on a computer has been proposed.

By the way, it has been considered to change the kind and the sensitivity of a scintillator according to the image generation conditions such as the physique of a patient and an image generation region in order to obtain a desired image quality even if the image generation conditions change. In such a case, a plurality of FPDs having scintillators of different kinds and different sensitivities from one another is used. Even though these FPDs are connected through the network described above, the kinds and the sensitivities of the scintillators in the FPDs cannot be recognized on the network when the situation is left as it is. Consequently, there is a possibility that the generation of a radiation image takes much time and the image generation becomes inefficient as a result. In particular, in the cassette type FPD, because the FPD can move if it is on a network, it is supposed that it takes much time to specify the kind and the sensitivity of a scintillator when the situation is left as it is.

SUMMARY OF THE INVENTION

It is an object of the invention to improve the efficiency in image generation by making it possible to recognize the kind and the sensitivity of a scintillator in an FPD.

In order to achieve the object, according to a first aspect of the invention, the radiation image generating system, comprises: a plurality of radiation image detecting apparatuses, each including at least a scintillator layer having a scintillator to emit light according to an entered radiation, a photoelectric conversion layer to detect the light emitted by the scintillator to convert the detected light into electric energy, and a switching element layer having switching elements to accumulate and output the electric energy obtained by the photoelectric conversion layer, the radiation image detecting apparatuses obtaining radiation image information of a subject; and a radiation image generating operation control apparatus including a selection section to select a desired radiation image detecting apparatus among the plurality of radiation image detecting apparatuses, wherein the radiation image generating operation control apparatus includes a display section to display scintillator information of the scintillator used in each of the plurality of radiation image detecting apparatuses.

According to a radiation image generating system of the first aspect of the invention, because the scintillator information of the scintillator used in each of the plurality of radiation image detecting apparatuses is displayed on the display section, a manager can recognize the kinds and the sensitivities of the scintillators of the radiation image detecting apparatuses connected to a network by viewing the scintillator information. Then, when the manager selects one radiation image detecting apparatus which is optimum for the image generation conditions (such as the physique of a patient and an image generation region) among the plurality of radiation image detecting apparatuses, even though the image generation conditions change, the manager can easily select the optimum radiation image detecting apparatus according to the changed conditions, and as a result the manager can effectively perform image generation in a desired quality.

In the radiation image generating system according to the first aspect of the invention, preferably, each of the radiation image detecting apparatuses has an identification information provided individually, and the display section of the radiation image generating operation control apparatus displays the scintillator information and the identification information.

According to such a radiation image generating system, it is possible to select a suitable radiation image detecting apparatus easily because of displaying both the scintillator information and the identification information at a time.

In accordance with the second aspect of the invention, the radiation image generating system, comprises: a plurality of radiation image detecting apparatuses, each including at least a scintillator layer having a scintillator to emit light according to an entered radiation, a photoelectric conversion layer to detect the light emitted by the scintillator to convert the detected light into electric energy, and a switching element layer having switching elements to accumulate and output the electric energy obtained by the photoelectric conversion layer, the radiation image detecting apparatuses obtaining radiation image information of a subject; a management apparatus to manage scintillator information of the scintillator in each of the plurality of radiation image detecting apparatuses; and a radiation image generating operation control apparatus to display the scintillator information managed by the management apparatus and to control a radiation image generating operation of one of the radiation image detecting apparatuses, corresponding to a selection result of a selection section to select one of the radiation image detecting apparatuses.

According to a radiation image generating system of a second aspect of the invention, because the scintillator information managed by the management apparatus is displayed on the radiation image generating operation control apparatus, a manager can recognize the kinds and the sensitivities of the scintillators of the radiation image detecting apparatuses connected to a network by viewing the scintillator information. Then, when one radiation image detecting apparatus which is optimum for the image generation conditions (such as the physique of a patient and a image generation region) is selected among the plurality of radiation image detecting apparatuses by a selection section, the radiation image generating operation control apparatus controls the radiation image generating operation of the selected radiation image detecting apparatus. Consequently, even though the image generation conditions change, the manager can easily select the optimum radiation image detecting apparatus according to the changed conditions, and as a result the manager can effectively perform image generation in a desired quality.

In the radiation image generating system according to the second aspect of the invention, preferably, each of the radiation image detecting apparatuses has an identification information provided individually, and the radiation image generating operation control apparatus displays the scintillator information and the identification information.

According to such a radiation image generating system, it is possible to select a suitable radiation image detecting apparatus easily because of displaying both the scintillator information and the identification information at a time.

In accordance with the third aspect of the invention, the radiation image generating system, comprises: a plurality of radiation image detecting apparatuses, each including at least a scintillator layer having a scintillator to emit light according to an entered radiation, a photoelectric conversion layer to detect the light emitted by the scintillator to convert the detected light into electric energy, and a switching element layer having switching elements to accumulate and output the electric energy obtained by the photoelectric conversion layer, the radiation image detecting apparatuses obtaining radiation image information of a subject; and a management apparatus to manage scintillator information of the scintillator in each of the plurality of radiation image detecting apparatuses, wherein each of the radiation image detecting apparatuses has an identification information provided individually, and the management apparatus has a linking section to link the scintillator information of the scintillator in each of the plurality of radiation image detecting apparatus with the identification information.

According to a radiation image generating system of a third aspect of the invention, the scintillator information and the identification information of the scintillator in each of the plurality of radiation image detecting apparatuses are linked with each other by the linking section. By reading the identification information through the management apparatus, the scintillator information of the radiation image detecting apparatus linked with the identification information can also be read. Thereby, it is enabled to recognize the kinds and the sensitivities of the radiation image detecting apparatuses connected to a network.

In the radiation image generating system of the third aspect, it is preferable to include a radiation image generating operation control apparatus which displays the scintillator information and the identification information linked with each other by the linking section and controls the radiation image generating operation of the radiation image detecting apparatus corresponding to a selection result of the selection section for selecting a radiation image.

Because the scintillator information managed by the management apparatus is displayed by the radiation image generating operation control apparatus, a manager can recognizing the kinds and the sensitivities of the scintillators of the radiation image detecting apparatuses connected to the network by viewing the scintillator information.

Moreover, when one radiation image detecting apparatus which is optimum for image generation conditions is selected by the selection section among the plurality of radiation image detecting apparatuses, the radiation image generating operation control apparatus controls the radiation image generating operation of the selected radiation image detecting apparatus. Consequently, even though the image generation conditions change, the radiation image detecting apparatus which is optimum according to the conditions can be easily selected, and as a result it becomes possible to perform image generation in a desired image quality.

In the radiation image generating system of the first to third aspect of the invention, preferably, the scintillator information includes at least one of kind and sensitivity of the scintillator.

As described above, it is suitable to change the kind and the sensitivity of a scintillator according to image generation conditions for obtaining a desired image quality even when image generation conditions (such as the physique of a patient and a image generation region) change. Consequently, as described above, if at least one of the kind and the sensitivity of a scintillator is included in the scintillator information, a radiation image detecting apparatus equipped with the optimum scintillator for the image generation conditions can be easily selected.

Preferably, the scintillator information includes at least one of kind and size of the radiation image detecting apparatus having the scintillator.

As described above, because at least one of the kind and the size of the radiation image detecting apparatus corresponding to a scintillator is included in the scintillator information, the radiation image detecting apparatus which is optimum for the image generation conditions can be selected also in consideration of the kind and the size of the radiation image detecting apparatus.

Preferably, in the radiation image generating system, the radiation image generating operation control apparatus displays the scintillator information in the plurality of radiation image detecting apparatuses at subject registration.

When the scintillator information in the plurality of radiation image detecting apparatuses is displayed at subject registration, the radiation image detecting apparatus equipped with the optimum scintillator to each patient can be selected.

Preferably, in the radiation image generating system, the radiation image generating operation control apparatus selects a candidate of the scintillator information which is adaptable to a image generation condition inputted at a subject reservation, and displays the scintillator information and other scintillator information in a way of distinguishing them visually to each other.

Because a candidate of the scintillator information suitable for the image generation conditions is selected and the selected candidate is displayed in a way of being visually distinguished from other scintillator information by the radiation image generating operation control apparatus, a radiographer can refer to the selection result judged from the objective viewpoint. Thereby, the individual difference of every radiographer at the time of judgment can be eliminated as much as possible.

Moreover, because the final judgment is left to the radiographer, an intention of the radiographer can be reflected. For example, it is also possible to ignore the scintillator information cited as the candidate, and to select other scintillator information when special image generation is performed.

Preferably, the radiation image generating system further comprises an image processing apparatus connected to a communication line, to perform image processing to the radiation image information obtained by the radiation image detecting apparatus, the image processing apparatus changing an image processing condition, corresponding to the scintillator information of the radiation image detecting apparatus having obtained the radiation image information.

Because the image processing apparatus alters the image processing conditions in a way of associating the image processing conditions with the scintillator information of the radiation image detecting apparatus from which the radiation image information has been obtained, it becomes possible to perform the optimum image processing corresponding to the scintillator of each radiation image detecting apparatus.

In the radiation image generating system, preferably, the radiation image generating operation control apparatus groups the plurality of radiation image detecting apparatuses in advance, and displays the scintillator information of the radiation image detecting apparatuses by every group.

Because the scintillator information in the radiation image detecting apparatuses is displayed by each group, troublesomeness can be suppressed when it is not necessary to refer to the scintillator information in all of the radiation image detecting apparatuses on a communication line.

BRIEF DESCRIPTION OF THE DRAWINGS

The present invention will become more fully understood from the detailed description given hereinafter and the accompanying drawings which are given by way of illustration only, and thus are not intended as a definition of the limits of the present invention, and wherein;

FIG. 3 is a block diagram showing the configuration of the principal part of a radiation image detecting apparatus constituting the radiation image generating system of FIG. 1;

FIG. 4 is a block diagram showing the configuration of the principal part of a console constituting the radiation image generating system of FIG. 1;

FIG. 5 is a block diagram showing the configuration of the principal part of a server constituting the radiation image generating system of FIG. 1; and FIG. 6 is a flowchart showing an example of the operation pertaining to the image generation processing by the radiation image generating system of FIG. 1.

THE PREFERRED EMBODIMENTS OF THE INVENTION

Figure 1:
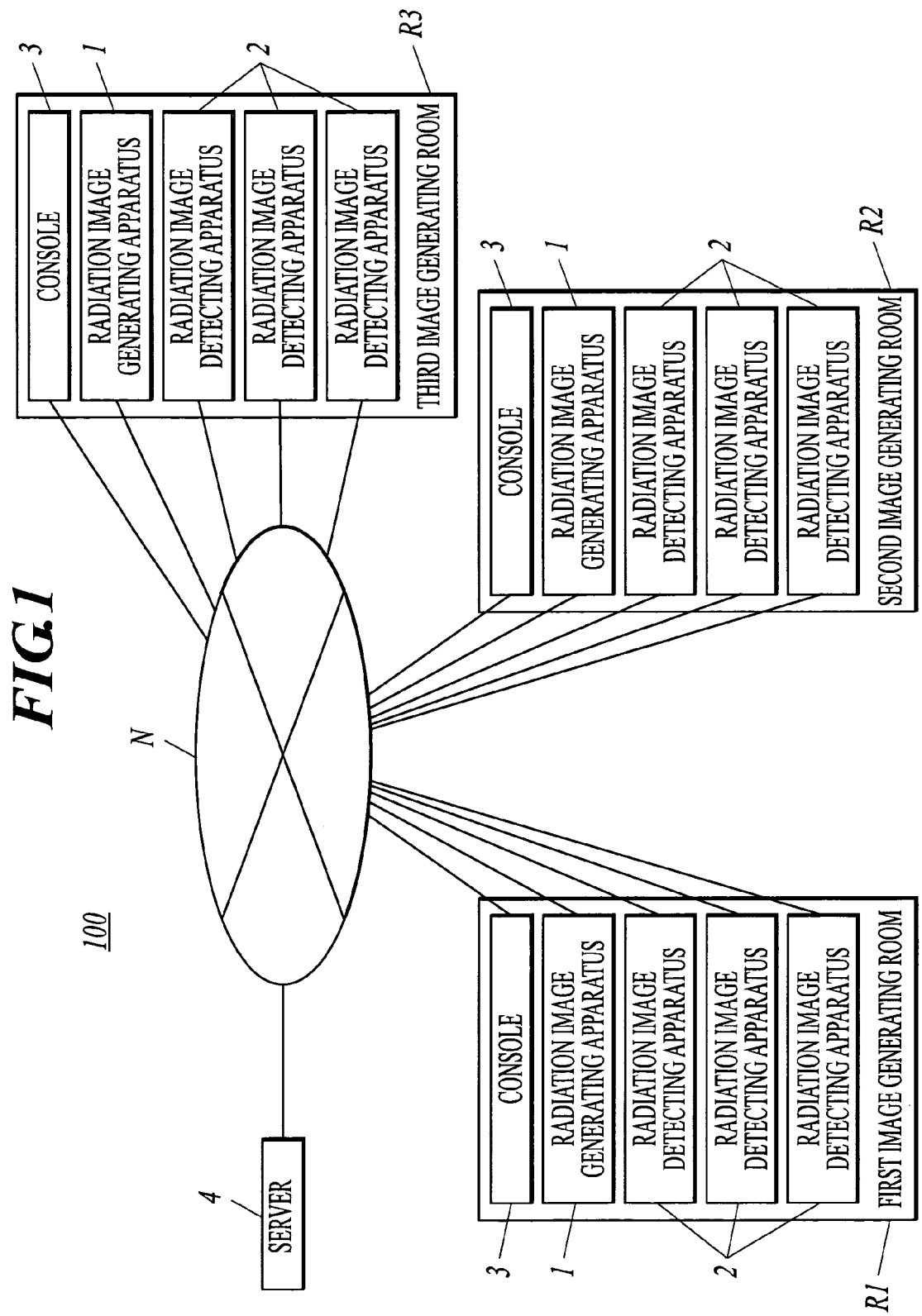
FIG. 1 is a view showing the schematic configuration of a radiation image generating system exemplified as an embodiment to which the invention is applied.

A preferred embodiment of the invention will be described in detail with reference to the attached drawings. FIG. 1 is a view showing a schematic configuration of a radiation image generating system exemplified as an embodiment to which the invention is applied.

As shown in FIG. 1, a radiation image generating system 100 includes three image generation rooms, that is, a first image generation room R1, a second image generation room R2 and a third image generation room R3. In each of the first, the second and the third image generation rooms R1, R2 and R3, there are installed a radiation image generation apparatus 1 which radiates a radiation such as an X-ray to a subject at the time of image generation the subject; a plurality of radiation image detecting apparatuses 2, each obtaining a radiation image of the subject; and a console 3 which performs control of the radiation image generating operations of the radiation image detecting apparatuses 2 which are installed in each of the image generation rooms R1, R2 and R3, display of a radiation image, image processing of a radiation image, and the like. Then, each apparatus in each of the image generation rooms R1, R2 and R3 is connected with one another through a network N. A management apparatus which manages all the radiation image detecting apparatuses 2 on the network N is connected to the network N.

Although the network N may be a communication line dedicated for the system here, it is preferable to be an existing line such as Ethernet (registered trademark) because the degree of freedom of the system configuration becomes low.

Figure 2:
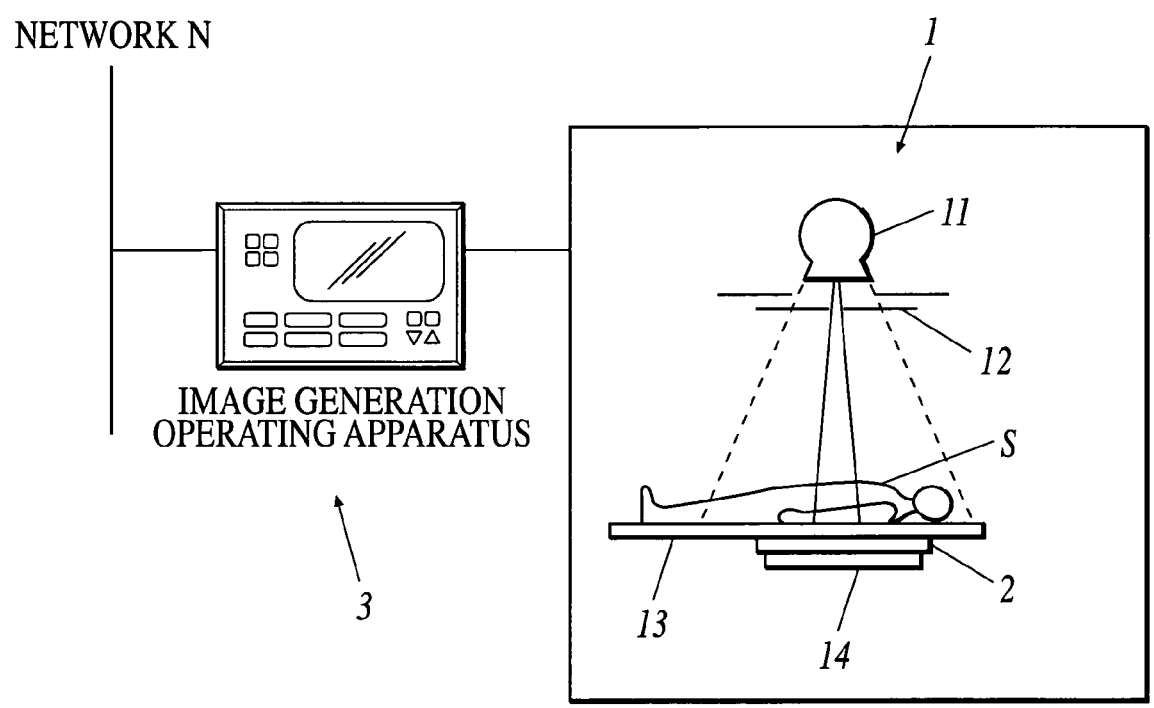
FIG. 2 is an explanatory view showing the configuration of the principal part of a radiation image generation apparatus 1 constituting the radiation image generating system of FIG. 1.

The radiation image generation apparatus 1 is described in detail with reference to FIG. 2. Here, FIG. 2 is an explanatory view showing the configuration of the principal part of the radiation image generation apparatus 1. The radiation image generation apparatus 1 is used to be installed in, for example, a image generation room in a hospital. The radiation image generation apparatus 1 includes a radiation source (radiation irradiating section) 11, and generates a radiation by applying a tube voltage to the radiation source 11. An iris device 12 which adjusts a radiation irradiating field is formed to enable freely opening and closing in a radiation irradiating hole of the radiation source 11. In a radiation irradiating range below the radiation source 11, a bed 13 on which a patient S is laid is provided, and a detecting apparatus attaching port (not shown) where a radiation image detecting apparatus 2 for reading the intensity of a radiation to detect a radiation image is attached, is formed below the bed 13. A photo-timer 14 is provided below the detecting apparatus attaching port, and the photo-timer 14 detects the dosage of the radiation which penetrates the patient S. When the dosage of the radiation which penetrates the patient S reaches a predetermined dosage, the photo-timer 14 is configured to transmit a signal to the console 3 so as to stop radiating the radiation from the radiation source 11.

In the following, each of the radiation image detecting apparatuses 2 is described in detail with reference to FIG. 3. FIG. 3 is a block diagram showing the configuration of the principal part of each of the radiation image detecting apparatuses 2.

For example, as shown in FIG. 3, the radiation image detecting apparatus 2 is a cassette type FPD housed in a cassette in the state in which a control unit 21, a RAM 22, a ROM 23, a detection unit 24, an image memory 25, a communication unit 26, a power source unit 27, a scintillator information memory 28 and the like are connected to one another with a bus A.

The random access memory (RAM) 22 is, for example, a volatile semiconductor memory, and constitutes a work area (not shown) and the like of various programs executed by the control unit 21.

The read only memory (ROM) 23 is a memory only for being read, in which, for example, various programs, identification information for identifying the radiation image detecting apparatus 2, and the like are stored.

The various programs include an obtainment control program for obtaining the radiation image information of a subject from the detection unit 24, an image storage control program for making the image memory 25 store the obtained radiation image information, a displaying information generation program for generating displaying image information outputted to the console 3 on the basis of the radiation image information, an association program for associating the displaying image information generated by the displaying information generation program with the radiation image information, a radiation image correction program for correcting the radiation image information, a displaying image correction program for correcting the displaying image information, a correction information obtaining program for obtaining correction information pertaining to the correction of the radiation image, a judgment program for judging whether the radiation image information may be transmitted to the console 3 or not, and the like.

The identification information is information which is given to each of the plurality of radiation image detecting apparatuses 2 for identifying each of them and is not overlapping with each other. The identification information includes a manufacturer's serial number, an ID number and the like.

The detection unit 24 includes at least a scintillator layer equipped with a scintillator for emitting light according to the intensity of a radiation which has entered into the scintillator from the radiation source 11 after having penetrated a subject, a photoelectric conversion layer for detecting emitted light from the scintillator to convert the detected light into electric energy, and a switching element layer equipped with switching elements such as thin film transistors (TFT's) which accumulates the electric energy obtained by the photoelectric conversion layer to output the accumulated electric energy.

The image memory 25 is configured to store the radiation image information which is obtained with the electric energy which is outputted from the switching elements of the detection unit 24 and is read under the control of the control unit 21. Concretely, the image memory 25 is composed of a nonvolatile memory such as a flash memory. The storage capacity of the image memory 25 is a size in which at least two radiation images can be stored. Incidentally, the upper limit of the storage capacity is suitably set according to the configuration and the like of the radiation image generating system 100. For example, the upper limit is a size in which about ten radiation images can be stored.

The communication unit 26 performs communication of various kinds of information with a console 3 and a server (management apparatus) 4 by a wireless communication system such as a wireless local area network (LAN). The communication unit 26 is configured to transmit (oroutput) reduced image information which was generated by the control unit 21 and which was provided with predetermined image correction, to the console 3. Further, the communication unit 26 is configured to transmit key information which establishes correspondences between the reduced image information which was generated by the control unit 21 and is transmitted to the console 3, and the radiation image information stored in the image memory 25 to the console 3. Then, the communication unit 26 is configured to output the radiation image information, which is stored in the image memory 25 and has received an image correction (which will be described later), to the console 3. The communication unit 26 is configured to receive a radiation image generating operation signal for controlling a radiation image generating operation from the console 3.

The power source unit 27 includes a rechargeable battery 271 for supplying power source to each unit constituting the radiation image detecting apparatus 2, and is configured to be possible to be charged through a charging terminal (not shown) which is provided at a predetermined position of the radiation image detecting apparatus 2.

The scintillator information memory 28 stores the scintillator information peculiar to the scintillator which is installed in the radiation image detecting apparatus 2, and is composed of, for example, a nonvolatile memory such as a flash memory. Here, in the scintillator information, at least one of the kind and the sensitivity (relative luminous intensity) of the scintillator is included. The kind of the scintillator includes the kinds of phosphors such as $Gd_2O_2S:Tb$ and CsI:Tl, which form a radiation light-converting layer. Preferably, at least one of the kind and the size of the radiation image detecting apparatus 2 corresponding to the scintillator is included in the scintillator information.

As the kind of the radiation image detecting apparatus 2, there are an FPD dedicated for a standing position and an FPD dedicated for a decubitus position in addition to the cassette type FPD exemplified in the embodiment.

As the size of the radiation image detecting apparatus 2, there are a 17×14 inch size, a 14×14 inch size, 11×14 inch size and the like.

The control unit 21 is composed of, for example, a central processing unit (CPU) or the like, and read a predetermined program stored in the ROM 23 to unwind the program in the work area of the RAM 22. Then, the control unit 21 executes various kinds of processing in accordance with the program. For example, the control unit 21 controls each switching element of the detection unit 24 on the basis of a radiation image generating operation signal transmitted from the console 3 while following an obtainment control program, and thereby the control unit 21 switches reading of the electric energy accumulated in the switching element to read the electric energy accumulated in the detection unit 24. Herewith, the control unit 21 obtains the radiation image information of a subject from the detection unit 24.

The control unit 21 makes the image memory 25 store the radiation image information obtained before new image generation of the subject according to an image storage control program.

With each obtaining radiation image information, the control unit 21 generates displaying image information outputted to the console 3 on the basis of the obtained radiation image information in accordance with the displaying information generation program. To put it concretely, as the displaying image information, the control unit 21 is configured to generate reduced image information having the information amount less than that of radiation image information. The reduction ratio of the reduced image is preferably one at which the length of each side becomes about ½ to 1/100 times of that of the original image (at which the number of pixels becomes about ¼ to 1/10000 times of that of the original image), and is more preferably one at which the length becomes about ¼ to 1/2500 times of that of the original image, for example.

Hereupon, the generation of a displaying image by the control unit 21 may be performed before storing of the radiation image information to the image memory 25, or may be performed after storing of the radiation image information.

Furthermore, the control unit 21 generates the key information for associating the displaying image information generated by the control unit 21 with the radiation image information stored in the image memory 25 in accordance with an association program.

The control unit 21 controls the communication unit 26 to transmit the identification information and the scintillator information to the server 4.

The control unit 21 corrects the obtained radiation image information in accordance with a radiation image correction program, or corrects the generated displaying image information in accordance with a displaying image correction program. To put it concretely, in the embodiment, a fixed pattern noise (FPN) correction for correcting the dark current accumulated in semiconductors such as amorphous silicon (a-Si) constituting the scintillator as time elapses, a white correction (gain correction) for correcting the dispersion of the gain of each pixel of the detection unit 24 are executed. In these image corrections, the control unit 21 follows the correction information obtaining program to obtain correction information pertaining to the correction of a radiation image. To put it concretely, for example, in the FPN correction, a dark current signal (FPN signal) is obtained, and in the white correction, white image data is obtained.

In the following, the FPN correction and the white correction are described more in detail.

The FPN correction is concretely an image correction for obtaining a true image signal by removing FPN signals included in an image signal obtained by image generation from the image signal as noises. Hereupon, an FPN signal is generally a function of temperature and accumulation time. Moreover, because the image generation time differs to every image generation region and every subject, an accumulation time of the detection unit 24 is measured at every image generation at the time of performing the FPN correction, and a dark current is accumulated in the state where no X-rays are radiated to the detection unit 24 for a time almost equal to the measured accumulation time after image generation. After that, by reading a signal from the detection unit 24, an FPN signal which is almost equal to the FPN signal included in the generated image is obtained. By subtracting the FPN image signal from an image signal obtained by radiographing (image-generating) the subject, the true image signal can be obtained.

Further, in the white correction, white image data (log value) is first subtracted from the image signal which has received log (logarithm) conversion after, for example, the FPN correction. Hereupon, the white image data is image data obtained by radiating a uniform radiation to the whole of the detection unit 24 without making any subject intervene. The obtained white image data is stored in a predetermined storage section. Incidentally, the obtainment of the white image data is periodically performed at, for example, every morning or once in a week.

The control unit 21 judges whether the radiation image information stored in the image memory 25 may be transmitted to the console 3 or not, on the basis of an image generation suitability signal which has been transmitted from a communication unit 36 of the console 3 and has been received by the control unit 21 through the communication unit 26 of the radiation image detecting apparatus 2 in accordance with the judgment program. To put it more concretely, the control unit 21 is configured to judge whether the radiation image information linked with the key information among a plurality of pieces of radiation image information stored in the image memory 25 may be transmitted to the console 3 or not, on the basis of the image generation suitability signal and the key information pertaining to the image generation suitability signal.

Next, the console 3 will be described with reference to FIG. 4. FIG. 4 is a block diagram showing the configuration of the principal part of the console 3.

The console 3 is a device of displaying a radiation image radiographed in the radiation image detecting apparatus 2, of performing predetermined image processing of the radiation image, and of controlling the radiation image generating operation of the radiation image detecting apparatus 2, in order that a radiographer may confirm whether image generation has been performed suitably or not. That is, the console 3 is used both as the radiation image generating operation control apparatus and the image processing apparatus in the invention. As shown in FIG. 4, the console 3 is composed of a control unit 31, a RAM 32, a ROM 33, a display unit 34, an operation input unit 35, a communication unit 36, a power source unit 37, an image storage unit 38 and the like. Each unit is connected with one another through a bus B.

The RAM 32 is, for example, a volatile semiconductor memory and constitutes a work area (not shown) and the like of various programs executed by the control unit 31. The RAM 32 is configured to store the reduced image information as a plurality of pieces of displaying image information outputted from the communication unit 26 of the radiation image detecting apparatus 2.

The ROM 33 is a memory only for being read, in which various programs to be executed by the control unit 31 are stored. The various programs include, for example, an image processing program for performing image processing of a radiation image, a control program for controlling the radiation image generating operation of the radiation image detecting apparatus 2 and the like.

Here, because the most suitable image processing conditions change according to the kinds of scintillators, a plurality of image processing programs or image processing parameters according to the kinds of the scintillators are stored in the ROM 33.

The control unit 31 is composed of, for example, a CPU or the like, and read a predetermined program stored in the ROM 33 to unwind the program in the work area of the RAM 32. Then, the control unit 31 executes various kinds of processing in accordance with the program. To put it concretely, the control unit 31 performs predetermined image processing such as the gradation processing, the frequency emphasis processing and the like, of an radiation image related to the radiation image information, on the basis of the radiation image information which has been transmitted from the communication unit 26 of the radiation image detecting apparatus 2 and has been received through the communication unit 36 in accordance with the image processing program.

The control unit 31 follows the control program while producing a radiation image generating operation signal on the basis of the operation signal from the operation input unit 35 to output the produced radiation image generating operation signal to the radiation image detecting apparatus 2 through the network N. The control unit 31 is configured to thereby control the radiation image generating operation of the radiation image detecting apparatus 2.

The display unit 34 is composed of, for example, a cathode ray tube (CRT), a liquid crystal display (LCD) and the like, to display various screens in accordance with an instruction of a display signal which has been outputted from the control unit 31 and has been inputted therein. To put it concretely, the display unit 34 is configured to be able to perform thumbnail display of a plurality of reduced images on the basis of a plurality of pieces of reduced image information which has been transmitted from the radiation image detecting apparatus 2 and has been received through the communication unit 36.

The display unit 34 is configured to display a radiation image generating operation instruction signal unit for instructing an input of a radiation image generating operation instruction signal at the time of a radiation image generating operation control of the radiation image detecting apparatus 2, an image generating suitability instruction unit for instructing, for example, an input of the image generation suitability signal in association with each reduced image at the time of a display of the reduce images, and the like. Here, the scintillator information of a radiation image detecting apparatus 2 is displayed in the radiation image generating operation instruction signal unit.

Then, the radiation image generating operation instruction unit and the image generating suitability instruction unit are displayed in the way of enabling the selection on the basis of, for example, a predetermined operation of the operation input unit 35.

The operation input unit 35 is composed of, for example, a keyboard, a mouse and the like, and outputs a depression signal of a key operated to be depressed with the keyboard or an operation signal of the mouse to the control unit 31 as an input signal. To put it concretely, the operation input unit 35 is constructed to output (input) an image display instruction signal related to a display instruction of a radiation image, a image generation suitability signal related to whether the image generating state of a radiation image is suitable or not, a radiation image generating operation instruction signal to the radiation image detecting apparatus 2, and the like.

The operation input unit 35 may be configured by using the so-called touch-sensitive panel for outputting positional information as an input signal, which is inputted by touching a transparent sheet panel covering the display screen of the display unit 34 with a finger or a dedicated stylus pen.

The communication unit 36 performs communication of various kinds of information with the communication unit 26 of the radiation image detecting apparatus 2 by a wireless LAN or the like, for example. To put it concretely, the communication unit 36 receives the reduced image information and the key information transmitted from the communication unit 26 of the radiation image detecting apparatus 2. The communication unit 36 transmits the radiation image generating operation instruction signal and the image generation suitability signal, both inputted by the operation input unit 35, and the key information linked to the reduced image information pertaining to the image generation suitability signal, to the radiation image detecting apparatus 2.

The power source unit 37 supplies power source to each unit constituting the console 3. The power source unit 37 may be configured to be equipped with, for example, a rechargeable battery capable of being charged through a predetermined charging terminal (not shown), or may be configured to be equipped with a power source connection unit to be connected with an AC commercial power source.

The image storage unit 38 is composed of, for example, a hard disk drive and the like, and constitutes an image database storing the radiation image information pertaining to a radiation image to which predetermined image processing is performed under the control of the control unit 31.

Next, the server 4 will be described with reference to FIG. 5. FIG. 5 is a block diagram showing the configuration of the principal part of a management apparatus.

The server 4 manages all the radiation image detecting apparatuses 2 on the network N. As shown in FIG. 5, the server 4 is composed of a control unit 41, a RAM 42, a ROM 43, a display unit 44, a operation input unit 45, a communication unit 46, a power source unit 47 and the like, and each unit is connected to one another with a bus C.

The RAM 42 is, for example, a volatile semiconductor memory, and constitutes a work area (not shown) of the various programs executed by the control unit 41, a storage area (not shown) storing the identification information and the scintillator information of a radiation image detecting apparatus 2.

The ROM 43 is a read-only memory, and stores various programs executed by the control unit 41 such as a control program for managing each of the radiation image detecting apparatuses 2.

The control unit 41 is composed of, for example, a CPU or the like, and reads a predetermined program stored in the ROM 43 to unwind the read program in the work area of the RAM 42. Then, the control unit 41 executes various pieces of processing in accordance with the program. To put it concretely, the control unit 41 is configured to manage each of the radiation image detecting apparatuses 2 on the basis of the identification information and the scintillator information of each of the radiation image detecting apparatuses 2 in accordance with the control program.

The communication unit 46 performs communication of various kinds of information with the radiation image detecting apparatus 2 by a wireless communication system such as the wireless LAN. To put it concretely, the communication unit 46 receives the identification information and the scintillator information, which have been outputted from the communication unit 26 of the radiation image detecting apparatus 2. Incidentally, the communication unit 46 transmits the identification information and the scintillator information when the server 4 manages the scintillator information and in the similar case.

The display unit 44 and the operation input unit 45 are configured to be almost the same as the display unit 34 and the operation input unit 35 included in the console 3.

The power source unit 47 supplies power source to each unit constituting the server 4.

Next, the image generating processing of a radiation image in the radiation image generating system 100 will be described with reference to FIG. 6. FIG. 6 is a flowchart showing an example of the operation related to the image generating processing by the radiation image generating system 100.

First, when a new radiation image detecting apparatus 2 is connected to the network N in each of image generation rooms R1, R2 and R3, from the communication unit 26 of the radiation image detecting apparatus 2, identification information and scintillator information are transmitted to the server 4 (Step S1). The control unit 41 of the server 4 manages the scintillator information of the radiation image detecting apparatus 2 connected to network N in accordance with a control program on the basis of the identification information and the scintillator information which have been obtained (Step S2). Hereupon, the server 4 manages all the radiation image detecting apparatuses 2 connected to the network N in the state of being grouped into each of the image generation rooms R1, R2 and R3. Incidentally, as the standard of grouping, not only the radiation image detecting apparatuses 2 are grouped into each of the image generation rooms R1, R2 and R3, but also the radiation image detecting apparatuses 2 may be grouped in a range including neighboring image generation rooms R1, R2 and R3.

After that, the control unit 31 of the console 3 obtains the group of the pieces of scintillator information corresponding to the image generation room R1, R2 or R3 of which the control unit 31 takes charge, from the server 4, and makes the display unit 34 display the scintillator information of all the radiation image detecting apparatuses 2 existing in the image generation rooms R1, R2 or R3 concerned (Step S3). Incidentally, when a radiation image detecting apparatus 2 which was once connected with the network N and its identification information and its scintillator information are registered is not connected to the network N, it is preferable to display also the fact which the radiation image detecting apparatus 2 is not connected to the network N now in the case where the scintillator information is displayed.

A radiographer performs the reservation of each patient on the basis of the scintillator information displayed on the display unit 34, and registers the subject (Step S4). At the time of the subject registration, the radiographer inputs image generation conditions such as the physique of the patient (such as a height, a weight and the like) and a image generating region into the console 3 by operating the operation input unit 35. On the basis of the inputted image generation conditions, the control unit 31 of the console 3 selects a candidate of the scintillator information adaptable to the image generation condition, and the control unit 31 makes the display unit 34 display the pieces of scintillator information in order that the scintillator information set as the candidate and the other scintillator information may be distinguished from one another visually. The radiographer refers to the scintillator information set as the candidate and the other scintillator information while selecting the radiation image detecting apparatus 2 equipped with the detection unit 24 which is the most suitable for the image generation conditions by operating the operation input unit 35, to input the selected radiation image detecting apparatus 2 into the console 3. That is, the operation input unit 35 is the selection section in the invention.

Incidentally, when there is no radiation image detecting apparatus 2 which is the most suitable for the image generation conditions in the group, the control unit 31 of the console 3 obtains the scintillator information in another group, and makes the display unit 34 display the obtained scintillator information thereon. Consequently, the optimum radiation image detecting apparatus 2 for the image generation conditions can be selected from the inside of the other group.

Thereafter, when an image generating start instruction is inputted to the console 3 (Step S5), the radiation image detecting apparatus 2 selected at Step S3 is set in the radiation image generation apparatus 1, and a radiation is radiated from the radiation image generation apparatus 1 to the subject. Then, the image generating of the subject is performed by using the radiation image detecting apparatus 2 (Step S6). That is, the scintillator layer of the detection unit 24 of the radiation image detecting apparatus 2 detects the radiation which has entered therein, and the photoelectric conversion layer converts the detected radiation into electric energy. Then, the switching element layer accumulates and reads the electric energy to obtain the radiation image information of the subject (Step S7).

To put it concretely, the control unit 21 reads the obtainment control program from the ROM 23, and rewinds the read obtainment control program in the RAM 22. Then, the control unit 21 controls each switching element of the detection unit 24 in accordance with the obtainment control program to switch the reading of the electric energy accumulated in each switching element. Thus, the control unit 21 reads all the electric energy accumulated in the detection unit 24.

Successively, the control unit 21 reads the radiation image correction program from the ROM 23, and unwinds the read radiation image correction program in the RAM 22. Then, the control unit 21 performs correction processing of an original image for processing a predetermined image correction to the obtained radiation image information in accordance with the radiation image correction program (Step S8).

After that, the control unit 21 reads the image storage control program from the ROM 23, and unwinds the read storage control program in the RAM 22. Then, the control unit 21 makes the image memory 25 store the radiation image information after the correction in accordance with the image storage control program (Step S9).

Next, the control unit 21 reads the displaying information generation program from the ROM 23, and unwinds the read displaying information generation program in the RAM 22. Then, the control unit 21 generates reduced image information having an information amount less than that of the radiation image information as a displaying image outputted to the console 3 on the basis of the obtained radiation image information in accordance with the displaying information generation program (Step S10).

Successively, the control unit 21 reads the displaying image correction program from the ROM 23, and unwinds the read displaying image correction program in the RAM 22. Then, the control unit 21 performs predetermined image correction to reduced image information in accordance with the displaying image correction program (Step S11).

The control unit is configured to perform generation and correction of the reduced image information at every obtainment of the radiation image information by the radiation image detecting apparatus 2.

Next, the control unit 21 reads the association program from the ROM 23, and unwinds the read association program in the RAM 22. Then, the control unit 21 generates the key information for associating the reduced image information transmitted to the console 3 and the radiation image information stored in the image memory 25 with each other in accordance with the association program (Step S12).

After that, the control unit 21 controls the communication unit 26 to make the communication unit transmit the generated reduced image information and the key information corresponding to the reduced image information, to the console 3 (Step S13).

When the console 3 receives the reduced image information and the key information, which are transmitted from the communication unit 26 of the radiation image detecting apparatus 2, through the communication unit 36, the control unit 31 of the console 3 stores the received reduced image information and the received key information in a predetermined region of the RAM 32 (Step S14).

After that, when an image display instruction signal pertaining to a display instruction of the reduced image information stored in the RAM 32 is inputted on the basis of the operation of the operation input unit 35, the control unit 31 obtains a plurality of pieces of reduced image information corresponding to the image display instruction signal from the RAM 32, and the control unit 31 makes the display unit 34 perform the thumbnail display of the plurality of reduced images on the basis of the reduced image information (Step S15). To put it concretely, the control unit 31 is configured to display the plurality of reduced images and image generating suitability instruction units linked with each of the reduced images, at predetermined positions of the display unit 34.

Then, when selection of a image generating suitability instruction unit displayed on the display unit 34 is instructed on the basis of a predetermined operation of the operation input unit 35 by the radiographer, an image generation suitability signal pertaining to whether the image generating state of the radiation image related to the selected image generating suitability instruction unit is inputted into the control unit 31 (Step S16).

The control unit 31 makes the inputted image generation suitability signal be once stored in the information storage area of the RAM 32 whenever the image generation suitability signal is inputted.

The key information received through the communication unit 36 is stored in, for example, the predetermined storage area in the RAM 32.

After that, when transmission of the image generation suitability signal to the radiation image detecting apparatus 2 is instructed in accordance with an operation of the operation input unit 35 by, for example, a radiographer, the control unit 31 reads the image generation suitability signal, transmission of which has been instructed, and the key information corresponding to the image generation suitability signals, from the RAM 32, and then the control unit 31 controls the communication unit 36 to transmit the read image generation suitability signal and the key information to the radiation image detecting apparatus 2 (Step S17).

When the radiation image detecting apparatus 2 receives the image generation suitability signal and the key information, which have been transmitted from the communication unit 36 of the console 3, through the communication unit 26, the control unit 21 reads the judgment program from the ROM 23 and unwinds the read judgment program in the RAM 22. Then, the control unit 21 judges whether or not the control unit 21 can transmit to the console 3 the radiation image information linked with the key information among the plurality of pieces of radiation image information stored in the image memory 25 on the basis of each of the image generation suitability signal and the key information in conformity with the judgment program (Step S18). To put it concretely, when a signal including an information indicating that the image generating state of the radiation image is suitable is inputted as the image generation suitability signal, the control unit 21 judges that the radiation image information can be transmitted. On the other hand, when a signal including the information indicating that the image generating state of the radiation image is unsuitable is inputted as the image generation suitability signal, the control unit 21 judges that it is unnecessary to transmit the radiation image information.

Hereupon, when it is judged that the radiation image information may be transmitted to the console 3 (Step S18; YES), the control unit 21 obtains radiation image information from the image memory 25, and makes the communication unit 26 transmit the obtained radiation image information to the console 3 (Step S19).

When the console 3 receives the radiation image information transmitted from the communication unit 26 of the radiation image detecting apparatus 2 through the communication unit 36, the control unit 31 of the console 3 reads the image processing program from the ROM 33, and unwinds the read image processing program in the RAM 32. Then the control unit 31 performs predetermined image processing such as a gradation processing and a frequency emphasis processing of the radiation image pertaining to the radiation image information on the basis of the received radiation image information in accordance with the image processing program (Step S21). At this time, the control unit 31 alters image processing conditions correspondingly to the scintillator information of the radiation image detecting apparatus 2 from which the radiation image information has been obtained. To put it concretely, the control unit 31 selects the optimum image processing program for the scintillator information among a plurality of image processing programs stored in the ROM 33, and performs image processing on the basis of the selected image processing program and the radiation image information.

After that, the control unit 31 stores the radiation image information after the image processing in a predetermined region of the image storage unit 38 (Step S22).

When it is judged that the radiation image information is not necessity to be transmitted to the console 3 at Step S18 (Step S18; NO), the control unit 21 controls each unit of the radiation image detecting apparatus 2 to shift to the reception state of the re-image generating of a radiation image (Step S20).

Here, the control unit 21 may be configured to delete data of the radiation image information unnecessary to be transmitted to the console 3.

As described above, according to the radiation image generating system 100 according to the embodiment of the invention, because the scintillator information managed by the server 4 is displayed in the console 3, a manager becomes possible to recognize the kinds and the sensitivities of the scintillators of the radiation image detecting apparatuses 2 connected to the network by viewing the scintillator information. Then, when one radiation image detecting apparatus 2 which is most suitable for the image generation conditions is selected among the plurality of radiation image detecting apparatuses 2, the console 3 controls the radiation image generating operation of the radiation image detecting apparatus 2. Consequently, even though the image generation conditions differ from one another, the optimum radiation image detecting apparatus 2 for the conditions can be easily selected, and it becomes possible to perform image generating in the desired image quality efficiently as a result.

Because at least one of the kinds and the sensitivities of the scintillators is included in the scintillator information, it is possible to easily select a radiation image detecting apparatus equipped with the optimum detection unit 24 for the image generation conditions. Furthermore, because at least one of the kind and the size of the radiation image detecting apparatus 2 corresponding to the detection unit 24 is include in the scintillator information, also in consideration of the kind and the size of the radiation image detecting apparatus 2, the optimum radiation image detecting apparatus 2 for the image generation conditions can be selected.

Moreover, because the scintillator information in a plurality of radiation image detecting apparatuses 2 is displayed at the time of subject registration (patient reservation), the radiation image detecting apparatus 2 equipped with the optimum scintillator to each patient can be selected.

Furthermore, because the candidate of suitable scintillator information is selected to image generation conditions and it is visually distinguished from other scintillator information to be displayed by the console 3, a radiographer can refer to the selection result judged in the objective viewpoint. Thereby, the individual difference by every radiographer at the time of judgment can be eliminated as much as possible. Moreover, because the final judgment is left to the radiographer, an intention of a radiographer can be reflected. For example, it is also possible for the radiographer to ignore the scintillator information cited as the candidate and to select other scintillator information when special image generating is performed.

Then, because the console 3 alters the image processing conditions correspondingly to the scintillator information of the radiation image detecting apparatus 2 from which radiation image information has been obtained, it becomes possible to perform the optimum image processing for the scintillator of each radiation image detecting apparatus 2.

Furthermore, because the scintillator information in the radiation image detecting apparatuses 2 is displayed for every group, troublesomeness can be suppressed when it is unnecessary to refer to the scintillator information in all the radiation image detecting apparatuses 2 on a communication line.

Incidentally, it is needless to say that the invention is not limited to the embodiment described above and can be modified suitably.

For example, although the scintillator information of each radiation image detecting apparatus 2 is collectively managed by the server 4 in the radiation image generating system 100 of the present embodiment, for example, the configuration in which the scintillator information of the radiation image detecting apparatus 2 which the console 3 takes charge of is stored in each of the console 3 of each of the image generation rooms R1, R2 and R3, and in which the scintillator information is obtained and managed by the server 4 as occasion demands can be adopted. That is, as long as the scintillator information itself can be always managed by the server 4, the scintillator information may be stored in the state of being collected at a position or may be stored in the state of being dispersed.

Moreover, although the configuration in which the server 4 is alone connected on network N has been described in the present embodiment, for example, one of the plurality of consoles 3 connected with the network N may operate as the management apparatus according to the invention. In such a case, because one console 3 functions as both of the radiation image generating operation control apparatus and the management apparatus of the invention, the system configuration can be simplified in comparison with the case where the management apparatus is installed alone.

Furthermore, in the present embodiment, although the case where the radiation image detecting apparatus 2 performs the corrections of the original image or the reduced image is exemplified to be described, the corrections of these images may be performed with the console 3. In such a case, the control unit 41 of the server 4 extracts the management information corresponding to the radiation image detecting apparatus 2 among a plurality of pieces of management information stored in the RAM 42 on the basis of the identification information of the radiation image detecting apparatus 2 used for image generating, and transmits the extracted management information to the console 3. The control unit 31 of the console 3 obtains the image correction data among the received management information, and performs the correction of an original image or a reduced image on the basis of the image correction data.

The embodiment is configured as follows. That is, the console 3 displays the scintillator information managed by the server 4, and a radiographer operates the operation input unit 35 on the basis of the displayed scintillator information to select the desired radiation image detecting apparatus 2 among the plurality of radiation image detecting apparatuses 2. However, the console 3 may directly display the scintillator information of the plurality of radiation image detecting apparatuses 2 on the display unit 34 without making the server 4 intervene. Even in such a case, because the scintillator information of the scintillator used for each of the plurality of radiation image detecting apparatuses 2 is displayed on the display unit 34, a manager can recognize the kinds and the sensitivities of the scintillators of the radiation image detecting apparatuses 2 connected to the network by viewing the scintillator information. Then, if one radiation image detecting apparatus 2 which is most suitable for image generation conditions is selected from a plurality of radiation image detecting apparatuses 2, though image generation conditions differ, in accordance with the conditions, the optimum radiation image detecting apparatus can be selected easily, and it becomes possible to perform image generating in a desired image quality efficiently as a result.

Although the wireless communication system is applied in the present embodiment, a cable communication system may be adopted.

In the embodiment, although the case where the scintillator information is previously stored in the radiation image detecting apparatuses 2 has been described, the scintillator information may not be stored in the radiation image detecting apparatuses 2. In this case, for example, all of the pieces of scintillator information of the radiation image detecting apparatuses 2 used on a network are beforehand registered in the server 4. Then, when a new image generating apparatus 2 is connected to the network, a manager selects the scintillator information agreeing with the scintillator used in the connected image generating apparatus 2 out of the operation input unit 45 of the server 4, and thereby the control unit 41 of the server 4 links the scintillator information with the image generating apparatus 2. That is, the control unit 41 of the server 4 is the linking section of the invention. Consequently, even if the scintillator information is not stored in the radiation image detecting apparatus 2, it is possible to read the scintillator information of the radiation image detecting apparatus 2 linked with the identification information also to display the read scintillator information on the display unit 34 when the identification information is read from the console 3 through the server 4. Herewith, it becomes possible to recognize the kinds and the sensitivities of the scintillators of the radiation image detecting apparatuses 2 connected to the network.

If the identification information and the scintillator information are registered in the server 4 from the beginning, even if thereafter the radiation image detecting apparatuses 2 is once disconnected from the network N and then connected to a different console 3 on the network, the cintillator information linked with the identification information of the radiation image detecting apparatus 2 can be read from the server 4, by the console 3.

The identification information or the scintillator information may be transmitted from the console 3 to the server 4 after it was transmitted to the console 3.

The entire disclosure of a Japanese Patent Application No. 2004-213,011, filed on Jul. 21, 2004, including specifications, claims, drawings and summaries are incorporated herein by reference in their entirety.

What is claimed is:

1. A radiation image generating system, comprising:
a plurality of radiation image detecting apparatuses, each including at least a scintillator layer having a scintillator to emit light according to an entered radiation, a photoelectric conversion layer to detect the light emitted by the scintillator to convert the detected light into electric energy, and a switching element layer having switching elements to accumulate and output the electric energy obtained by the photoelectric conversion layer, the radiation image detecting apparatuses obtaining radiation image information of a subject; and
a radiation image generating operation control apparatus including a selection section to select a desired radiation image detecting apparatus among the plurality of radiation image detecting apparatuses, wherein the radiation image generating operation control apparatus includes a display section to display scintillator information of the scintillator used in each of the plurality of radiation image detecting apparatuses.

2. The radiation image generating system of claim 1, wherein each of the radiation image detecting apparatuses has an identification information provided individually, and the display section of the radiation image generating operation control apparatus displays the scintillator information and the identification information.

3. The radiation image generating system of claim 2, wherein the scintillator information includes at least one of kind and sensitivity of the scintillator.

4. The radiation image generating system of claim 3, wherein the scintillator information includes at least one of kind and size of the radiation image detecting apparatus having the scintillator.

5. The radiation image generating system of claim 1, wherein the radiation image generating operation control apparatus displays the scintillator information in the plurality of radiation image detecting apparatuses at subject registration.

6. The radiation image generating system of claim 1, wherein the radiation image generating operation control apparatus selects a candidate of the scintillator information which is adaptable to an image generation condition inputted at a subject reservation, and displays the scintillator information and other scintillator information in a way of distinguishing them visually to each other.

7. The radiation image generating system of claim 1, further comprising an image processing apparatus connected to a communication line, to perform image processing to the radiation image information obtained by the radiation image detecting apparatus, the image processing apparatus changing an image processing condition, corresponding to the scintillator information of the radiation image detecting apparatus having obtained the radiation image information.

8. The radiation image generating system of claim 1, wherein the radiation image generating operation control apparatus groups the plurality of radiation image detecting apparatuses in advance, and displays the scintillator information of the radiation image detecting apparatuses by every group.

9. A radiation image generating system, comprising:
a plurality of radiation image detecting apparatuses, each including at least a scintillator layer having a scintillator to emit light according to an entered radiation, a photoelectric conversion layer to detect the light emitted by the scintillator to convert the detected light into electric energy, and a switching element layer having switching elements to accumulate and output the electric energy obtained by the photoelectric conversion layer, the radiation image detecting apparatuses obtaining radiation image information of a subject;
a management apparatus to manage scintillator information of the scintillator in each of the plurality of radiation image detecting apparatuses; and
a radiation image generating operation control apparatus to display the scintillator information managed by the management apparatus and to control a radiation image generating operation of one of the radiation image detecting apparatuses, corresponding to a selection result of a selection section to select one of the radiation image detecting apparatuses.

10. The radiation image generating system of claim 9, wherein each of the radiation image detecting apparatuses has an identification information provided individually, and the radiation image generating operation control apparatus displays the scintillator information and the identification information.

11. The radiation image generating system of claim 10, wherein the scintillator information includes at least one of kind and sensitivity of the scintillator.

12. The radiation image generating system of claim 11, wherein the scintillator information includes at least one of kind and size of the radiation image detecting apparatus having the scintillator.

13. The radiation image generating system of claim 9, wherein the radiation image generating operation control apparatus displays the scintillator information in the plurality of radiation image detecting apparatuses at subject registration.

14. The radiation image generating system of claim 9, wherein the radiation image generating operation control apparatus selects a candidate of the scintillator information which is adaptable to a image generation condition inputted at a subject reservation, and displays the scintillator information and other scintillator information in a way of distinguishing them visually to each other.

15. The radiation image generating system of claim 9, further comprising an image processing apparatus connected to a communication line, to perform image processing to the radiation image information obtained by the radiation image detecting apparatus, the image processing apparatus changing an image processing condition, corresponding to the scintillator information of the radiation image detecting apparatus having obtained the radiation image information.

16. The radiation image generating system of claim 9, wherein the radiation image generating operation control apparatus groups the plurality of radiation image detecting apparatuses in advance, and displays the scintillator information of the radiation image detecting apparatuses by every group.

17. A radiation image generating system comprising:
a plurality of radiation image detecting apparatuses, each including at least a scintillator layer having a scintillator to emit light according to an entered radiation, a photoelectric conversion layer to detect the light emitted by the scintillator to convert the detected light into electric energy, and a switching element layer having switching elements to accumulate and output the electric energy obtained by the photoelectric conversion layer, the radiation image detecting apparatuses obtaining radiation image information of a subject; and
a management apparatus to manage scintillator information of the scintillator in each of the plurality of radiation image detecting apparatuses,
wherein each of the radiation image detecting apparatuses has an identification information provided individually, and the management apparatus has an linking section to link the scintillator information of the scintillator in each of the plurality of radiation image detecting apparatus with the identification information.

18. The radiation image generating system of claim 17, wherein a radiation image generating operation control apparatus to display the scintillator information linked by the linking section and to control a radiation image generating operation of one of the radiation image detecting apparatuses, corresponding to a selction result of a selection section to select one of the radiation image detecting apparatuses.

19. The radiation image generating system of claim 18, wherein the radiation image generating operation control apparatus displays the scintillator information in the plurality of radiation image detecting apparatuses at subject registration.

20. The radiation image generating system of claim 18, wherein the radiation image generating operation control apparatus selects a candidate of the scintillator information which is adaptable to a image generation condition inputted at a subject reservation, and displays the scintillator information and other scintillator information in a way of distinguishing them visually to each other.

21. The radiation image generating system of claim 17, wherein the scintillator information includes at least one of kind and sensitivity of the scintillator.

22. The radiation image generating system of claim 21, wherein the scintillator information includes at least one of kind and size of the radiation image detecting apparatus having the scintillator.

23. The radiation image generating system of claim 17, further comprising an image processing apparatus connected to a communication line, to perform image processing to the radiation image information obtained by the radiation image detecting apparatus, the image processing apparatus changing an image processing condition, corresponding to the scintillator information of the radiation image detecting apparatus having obtained the radiation image information.

24. The radiation image generating system of claim 17, wherein the radiation image generating operation control apparatus groups the plurality of radiation image detecting apparatuses in advance, and displays the scintillator information of the radiation image detecting apparatuses by every group.

* * * * *